(12) United States Patent
Liu et al.

(10) Patent No.: US 8,951,929 B2
(45) Date of Patent: Feb. 10, 2015

(54) CATALYST PREPARATION AND METHODS OF USING SUCH CATALYSTS

(75) Inventors: Yan Liu, Singapore (SG); Toru Nishimura, Singapore (SG)

(73) Assignees: Agency for Science, Technology and Research, Connexis (SG); Mitsui Chemicals Inc., Tokyo (JP)

(*) Notice: Subject to any disclaimer, the term of this patent is extended or adjusted under 35 U.S.C. 154(b) by 517 days.

(21) Appl. No.: 12/808,781

(22) PCT Filed: Jan. 16, 2008

(86) PCT No.: PCT/SG2008/000018
§ 371 (c)(1),
(2), (4) Date: Jun. 17, 2010

(87) PCT Pub. No.: WO2009/091336
PCT Pub. Date: Jul. 23, 2009

(65) Prior Publication Data
US 2010/0285948 A1  Nov. 11, 2010

(51) Int. Cl.
*B01J 29/06* (2006.01)
*C07C 2/76* (2006.01)
*B01J 29/076* (2006.01)
*B01J 29/48* (2006.01)
*B01J 29/78* (2006.01)
*B01J 29/90* (2006.01)
*B01J 38/04* (2006.01)
*C10G 45/68* (2006.01)

(52) U.S. Cl.
CPC ............ *B01J 29/076* (2013.01); *B01J 29/48* (2013.01); *B01J 29/7876* (2013.01); *B01J 29/90* (2013.01); *B01J 38/04* (2013.01); *C07C 2/76* (2013.01); *C10G 45/68* (2013.01); *B01J 2229/186* (2013.01); *B01J 2229/34* (2013.01); *B01J 2229/40* (2013.01); *C07C 2529/48* (2013.01)
USPC ............. 502/60; 502/74; 502/77; 502/85; 502/34; 585/415; 585/417

(58) Field of Classification Search
USPC ............ 502/60, 74, 77, 85, 34; 585/415, 417
See application file for complete search history.

(56) References Cited

U.S. PATENT DOCUMENTS

| 6,093,671 | A | 7/2000 | Wu et al. | |
| 6,552,243 | B2* | 4/2003 | Allison et al. | 585/417 |
| 2001/0008949 | A1 | 7/2001 | Wu et al. | |
| 2003/0144565 | A1* | 7/2003 | Allison et al. | 585/418 |
| 2007/0249740 | A1* | 10/2007 | Iaccino et al. | 518/726 |
| 2007/0249879 | A1* | 10/2007 | Iaccino et al. | 585/418 |
| 2008/0312483 | A1 | 12/2008 | Ichikawa et al. | |

FOREIGN PATENT DOCUMENTS

| JP | A-11-060514 | 3/1999 |
| JP | A-2004-269398 | 9/2004 |
| JP | A-2005-255605 | 9/2005 |
| JP | A-2005-343879 | 12/2005 |
| WO | WO 2005/028105 | 3/2005 |
| WO | WO 2006/011568 | 2/2006 |

OTHER PUBLICATIONS

Liu et al. (2005) Applied Catalysis A: General 295:79-88, "Methane dehydroaromatization over Mo/HZSM-5 calalysts: The reactivity of $MoC_x$ species formed from $MoO_x$ associated and non-associated with Brönsted acid sites".
Shu et al. (1997) Journal of Catalysis 170:11-19, "Promotional Effect of Ru on the Dehydrogenation and Aromatization of Methane in the Absence of Oxygen over Mo/HZSM-5 Catalysts".
Solymosi et al. (1996) Catalysis Letters 39:157-161, "Conversion of methane to benzene over $Mo_2C$ and $Mo_2C$/ZSM-5 catalysts".
Wang et al. (1993) Catalysis Letters 21:35-41, "Dehydrogenation and aromatization of methane under non-oxidizing conditions".
Wang et al. (1997) Journal of Catalysis 169:347-358, "Characterization of Mo/ZSM-5 Catalyst for the Conversion of Methane Benzene".
Xu et al. (2003) Journal of Catalysis 216:386-395, "Direct conversion of methane under non-oxidative conditions".
International Search Report and Written Opinion mailed Mar. 28, 2008 in PCT/SG2008/000018.
International Preliminary Report on Patentability mailed Oct. 14, 2009 in PCT/SG2008/000018.

* cited by examiner

Primary Examiner — Elizabeth Wood
(74) Attorney, Agent, or Firm — Swanson & Bratschun, L.L.C.

(57) ABSTRACT

A process for the pre-treatment of Mo/ZSM-5 and Mo/MCM-22 catalysts is provided, which process comprises heating the catalyst at 500° C. in the presence of propane. The treated catalyst, when used in the non-oxidative dehydrogenation of methane demonstrates improved benzene yield and catalyst stability as compared to catalysts pre-treated with He, methane or $H_2$.

25 Claims, No Drawings

CATALYST PREPARATION AND METHODS OF USING SUCH CATALYSTS

RELATED APPLICATIONS

This application is a 35 U.S.C. §371 national phase application of PCT/SG2008/000018 (WO 2009/091336) filed Jan. 16, 2008, entitled "Catalyst Preparation and Methods of Using Such Catalysts", which is incorporated herein by reference in its entirety.

FIELD OF THE INVENTION

The present invention is concerned with methane dehydroaromatization catalysts, in particular Mo/ZSM-5 and Mo/MCM-22 catalysts, and methods of preparing and using such catalysts.

BACKGROUND TO THE INVENTION

There is considerable interest in exploiting natural gas (predominantly comprising methane) as a feed stock for the formation of higher hydrocarbons, not least because of finite oil reserves.

Several alternative approaches to the use of methane as a starting material have been explored. Firstly, conversion, via steam reforming, of methane to synthesis gas (CO and $H_2$) followed by formation of methanol or hydrocarbons from catalysed reaction of synthesis gas (e.g. via the Fischer-Tropsch process). This approach may be chemically feasible but the energy requirements are considerable and commercialisation of this technology has not been widespread.

Secondly, aromatization of methane in the presence of an oxidising species has been used to form benzene and other aromatic hydrocarbons. Despite initial enthusiasm for oxidative dehydroaromatization, limitations in terms of C2 yield and selectivity have prevented commercial implementation.

Thirdly, aromatization of methane has been studied in non-oxidising conditions. Such non-oxidising conditions make the formation of benzene considerably less thermodynamically favourable than in the corresponding oxidative process. Thus, such a process is inherently difficult to perform on a scale that would be attractive for commercialisation. Molybdenum-containing aluminosilicates, particularly Mo/ZSM-5 and Mo/MCM-22, have been shown to be the most promising candidates for conversion of methane to benzene in a non-oxidative environment, but even these have significant drawbacks. In particular, reported results (L. Wang, L. Tao, M. Xie, G. Xu, J. Huang, Y. Xu, Catal. Lett. 21 (1993) 35; Y. Xu, S. Liu, L. Wang, M. Xie, X. Guo, Catal. Lett. 30 (1995) 135; F. Solymosi, A. Erdohelyi, A. Szoke, Catal. Lett. 32 (1995) 43; S. Wong, Y. Xu, W. Liu, L. Wang, X. Guo, Appl. Catal. A 136 (1996) 7; L. Chen, L. Lin, Z. Xu, T. Zhang, X. Li, Catal. Lett. 39 (1996) 169; D. Wang, J. H. Lunsford, M. P. Rosynek, Top. Catal. 3 (1996) 289; L. Wang, Y. Xu, S. Wong, W. Cui. X. Guo, Appl. Catal. A 152 (1997) 173; S. Liu, Q. Dong, R. Ohnishi, M. Ichikawa, Chem. Commun., 1997, 1445; F. Solymosi, J. Cserenyi, A. Szoke, T. Bansagi, A. Uszko, J. Catal. 165 (1997) 150; D. Wang, J. H. Lunsford, M. P. Rosynek, J. Catal. 169 (1997) 347; Y. Shu, Y. Xu, S. Wang, L. Wang, X. Guo, J. Catal. 170 (1997) 11; S. Liu, L. Wang, R. Ohnishi, m. Ichikawa, J. Catal. 181 (1999) 175 and Y. Xu, X. Bao, L. Lin, J. Catal. 216 (2003) 386) for methane conversion are low. Furthermore, poor catalyst stability, likely due at least in part to coke formation, means that commercialisation of this technology has not occurred.

Thus, at present, methane dehydroaromatization represents a potentially useful route to synthesis of higher hydrocarbons but significant problems exist with the technology such that commercialisation is not envisaged. In particular, the suppression of fast deactivation of the catalyst due to coke formation is a challenge that must be addressed before industrial application.

SUMMARY OF THE INVENTION

The present inventors have identified a new process for improving catalyst stability of catalysts used for non-oxidative methane dehydroaromatization and in doing so have made a valuable contribution to the development of non-oxidative methane dehydroaromatization as an alternative to oil-based processes.

At its most general, the present invention proposes that a non-oxidative methane dehydroaromatization catalyst should be prepared from a catalyst precursor by heating the catalyst precursor in the presence of propane. This has been found by the present inventors to provide a surprising improvement in catalyst stability. Improved conversion rates of the methane feedstock can also be obtained as a result of the pre-treatment. In embodiments, selectivity for benzene is also improved, as compared to catalysts prepared without such pre-treatment.

In a first aspect, the present invention provides a process for preparing a methane dehydroaromatization catalyst comprising the step of heating a catalyst precursor comprising molybdenum and an aluminosilicate at a temperature of at least 300° C. in the presence of a treatment gas, wherein the treatment gas comprises propane.

The step of heating the catalyst precursor in the presence of a treatment gas comprising propane is referred to herein as the "pre-treatment step" or "pre-treatment". The product formed by heating the catalyst precursor in the presence of propane is referred to herein as the "catalyst". Where reference is made herein to a catalyst that has not undergone pre-treatment, it is referred to as an "untreated catalyst".

The present invention therefore provides a pre-treatment process, the product of which is a catalyst that is adapted to catalyse the non-oxidative dehydroaromatization of methane. In particular, the pre-treatment step changes the catalyst precursor such that the rate of catalyst deactivation of the catalyst can be reduced, as compared to an untreated catalyst (or pre-treatment using a different treatment gas, such as helium).

Surprisingly, the present inventors have found that the pre-treatment step provides the advantages discussed above independently of the nature of the aluminosilicate. Thus, for example, as discussed herein, both molybdenum-containing ZSM-5 and MCM-22 benefit from the pre-treatment step.

Suitably the catalyst precursor comprises molybdenum supported on an aluminosilicate. Alternatively, the molybdenum and aluminosilicate may be present as a mixture.

Preferably the aluminosilicate is a zeolite. Preferably the zeolite is selected from zeolites having a framework type MFI and zeolites having a framework type MWW. Particularly preferred zeolites are ZSM-5 (framework type MFI) and MCM-22 (framework type MWW).

Preferably the catalyst precursor is selected from Mo/ZSM-5 and Mo/MCM-22.

The Si/2Al ratio of the aluminosilicate is suitably in the range 10 to 100, preferably 15 to 50.

Preferably some or all of the molybdenum in the catalyst precursor is present in the form of an oxide. Suitably at least half, based on the total number of molybdenum ions in the catalyst precursor, preferably substantially all, more preferably all, of the molybdenum is in the form of an oxide. A preferred form of oxide is $MoO_3$. Indeed, the catalyst precursor may be formed from a mixture of $MoO_3$ and aluminosilicate or from $MoO_3$ supported on aluminosilicate. Molybdenum oxide may also be in the form of $MoO_4^{2-}$ or $Mo_7O_{24}^{6-}$.

A particularly preferred catalyst precursor comprises one or both of $MoO_3$/ZSM-5 and $MoO_3$/MCM-22.

Preferably some or all of the molybdenum in the catalyst precursor is present as $Mo^{6+}$. Suitably at least half, based on the total number of molybdenum ions in the catalyst, preferably substantially all, more preferably all, of the molybdenum is present as $Mo^{6+}$.

In other embodiments, the catalyst precursor is a used catalyst such that the process is a re-activation process. Suitably, the used catalyst has been used in a methane dehydroaromatization reaction. Typically, such a catalyst will comprise coke deposits, as discussed herein.

The amount of molybdenum, expressed as a percentage of the total weight of the catalyst precursor, is suitably at least 1%, preferably at least 2%, more preferably at least 5% and most preferably at least 10%.

Particularly preferred amounts of molybdenum are in the range 1 to 20%, more preferably 2 to 15%, more preferably 5 to 15%, more preferably 10 to 15%, more preferably 11 to 13% and most preferably about 12%.

It is preferred that the catalyst precursor includes a promoter. Such a promoter suitably comprises a transition metal, with preferred examples being one or more of Ga, Zn, Nb, Zr, La, Co, Fe, Ce, Ag, Y, V, Sr, W, Yb, Sm, Ni, Ru, Rh, Pt, Cu, Au, Al, Ti, Pb, Re, Ir, Si, Sn and Pd. Particularly preferred promoters are Ga, Zn, Zr, Fe, W, Cu and Pd.

The amount of promoter can be selected in order to optimise methane conversion and selectivity for benzene. Nevertheless, preferably the promoter is present in an amount of at least 0.1%, expressed as a percentage of the total weight of the catalyst precursor. Suitably, the promoter is present in an amount of at least 0.5%, preferably at least 0.8% and most preferably at least 1%.

A particularly preferred range for the amount of promoter is 0.5% to 10%, more preferably 0.5 to 5%, more preferably 0.8 to 4%, more preferably 0.8 to 3.5% and most preferably 1 to 3%.

One or more promoters can be used. For example, two or three different promoters can be used.

The particle size, surface area and other properties of the catalyst precursor can be selected in the normal way and in accordance with the skilled reader's common general knowledge.

The pre-treatment step suitably causes a change in the structure of the catalyst precursor such that the catalyst produced by the pre-treatment is particularly suitable for methane dehydroaromatization, especially non-oxidative dehydroaromatization. Indeed, catalysts produced in embodiments of the pre-treatment process have different physical/chemical characteristics compared to the respective catalyst precursor. For example, molybdenum oxide changes as a result of pre-treatment. In particular, molybdenum oxide is preferably reduced by the pre-treatment. The presence of molybdenum oxide can be detected by XRD. Thus, suitably peaks attributable to molybdenum oxide in the catalyst precursor are substantially reduced and preferably not visible after pre-treatment. It is believed that the change in physical/chemical characteristics is responsible for the improved performance, in the non-oxidative dehydroaromatization of methane, of the catalyst, as compared to untreated catalysts. In this connection, the present inventors have found propane, when used in accordance with the present invention, to be reactive enough to convert molybdenum oxides to molybdenum carbides.

In particular, the catalyst preferably provides a benzene yield, as measured in accordance with the methods disclosed herein, of at least 2%, more preferably at least 3%, more preferably at least 3.5%, more preferably at least 4%, more preferably at least 4.2%, more preferably at least 4.5%, more preferably at least 5%, more preferably at least 5.2%, more preferably at least 5.5%, and more preferably at least 6%.

Suitably the catalyst has improved stability as compared to a catalyst precursor that did not undergo the pre-treatment. Preferably the catalyst has an Activity Preservation Ratio (APR), as measured in accordance with the methods disclosed herein, of at least 40%, more preferably at least 50%, more preferably at least 55%, more preferably at least 60%, more preferably at least 65%, more preferably at least 70%, more preferably at least 75%, and most preferably at least 80%.

Suitably the duration of the pre-treatment step is at least 10 minutes, preferably at least 20 minutes.

Preferably, the duration of the pre-treatment step is 200 minutes or less, more preferably 100 minutes or less, more preferably 70 minutes or less, more preferably 60 minutes or less, more preferably 50 minutes or less, and most preferably 40 minutes or less.

A particularly preferred duration of the pre-treatment step is 10 to 100 minutes, more preferably 20 to 40 minutes and most preferably about 30 minutes.

These short pre-treatment times provide considerable economic benefits, particularly with reference to the reduction in energy required to prepare the catalyst. Thus, the pre-treatment step of the present invention enables a reduced preparation time as compared to known methods of pre-treating or activating methane dehydroaromatization catalysts, whilst preserving or improving catalyst stability.

Suitably the pre-treatment step occurs at a temperature of at least 300° C., more preferably at least 400° C., more preferably at least 450° C., more preferably at least 475° C., more preferably at least 490° C. and most preferably at least 500° C.

Suitably the pre-treatment step occurs at a temperature of less than 700° C., more preferably less than 650° C., more preferably less than 600° C., more preferably less than 550° C., more preferably less than 525° C., and most preferably less than 510° C. The present inventors have found that at higher pre-treatment temperatures, fast coke formation can occur.

The upper and lower limits referred to above may be combined in any combination to give a range. Particularly preferred ranges for the pre-treatment temperature are at least 300° C. to less than 700° C., more preferably at least 400° C. to less than 700° C., more preferably 450° C. to 650° C., more preferably 475° C. to 600° C., more preferably 475° C. to 550° C., more preferably 475° C. to 525° C. and most preferably 490° C. to 510° C. A temperature of about 500° C. is particularly preferred.

Suitably the treatment gas is supplied to the catalyst precursor so as to provide a flow of treatment gas. The skilled reader is able to select appropriate flow rates for the treatment gas, based on the reactor design, the amount of catalyst precursor and the form of the catalyst precursor.

For guidance, in a continuous fixed bed flow reactor with a catalyst precursor charge of 300 mg, a flow rate of 8 ml/min of treatment gas (100% propane) was found to provide excellent results.

Suitably, for at least some of the pre-treatment step, the pressure of the treatment gas is in the range 0.05 MPa to 5

MPa, preferably in the range 0.1 MPa to 1 MPa. A pressure of about 0.1 MPa (atmospheric pressure) is particularly preferred.

Suitably the pressure of the treatment gas is within the range referred to above, and suitably the preferred range referred to above, for at least half of the pre-treatment step, preferably for substantially all, most preferably for all of the pre-treatment step.

It is preferred that at the start of the pre-treatment step, the pressure of the treatment gas is within the above range, and suitably the preferred range referred to above.

The treatment gas may comprise one or more gases in addition to propane.

Other gases that may be used in combination with propane include one or more selected from $H_2$, $CH_4$, He, Ar, $C_2H_6$, $C_4H_{10}$, $NH_3$ and $N_2$.

However, it is preferred that the treatment gas comprises at least 50 mol % propane. Preferably the treatment gas comprises at least 75 mol %, more preferably at least 85 mol %, more preferably at least 95 mol % and more preferably at least 99 mol % propane. In particularly preferred embodiments, the treatment gas consists substantially of, preferably consists essentially of and most preferably consists of propane.

Unless stated otherwise, pre-treatment in the presence of the treatment gas means pre-treatment in the absence of any other gas.

In particularly preferred embodiments, the present invention provides a process for preparing a methane dehydroaromatization catalyst comprising the step of heating a catalyst precursor comprising Mo/ZSM-5 or Mo/MCM-22 at a temperature in the range of 450° C. to 550° C. in the presence of a treatment gas, wherein the treatment gas comprises propane.

In even more preferred embodiments, the present invention provides a process for preparing a methane dehydroaromatization catalyst comprising the step of heating a catalyst precursor comprising Mo/ZSM-5 or Mo/MCM-22 at a temperature in the range of 450° C. to 550° C. for about 10 to 50 minutes in the presence of a treatment gas, wherein the treatment gas comprises propane.

In even more preferred embodiments, the present invention provides a process for preparing a methane dehydroaromatization catalyst comprising the step of heating a catalyst precursor comprising Mo/ZSM-5 or Mo/MCM-22 at a temperature in the range of 450° C. to 550° C. for about 10 to 50 minutes in the presence of a treatment gas, wherein the treatment gas consists essentially of propane.

In even more preferred embodiments, the present invention provides a process for preparing a methane dehydroaromatization catalyst comprising the step of heating a catalyst precursor comprising Mo/ZSM-5 or Mo/MCM-22 at a temperature in the range of 450° C. to 550° C. for about 10 to 50 minutes in the presence of a treatment gas, wherein Mo is present in an amount of at least 10 wt % based on the total weight of the catalyst precursor and the treatment gas consists essentially of propane.

In the most preferred embodiments, the present invention provides a process for preparing a methane dehydroaromatization catalyst comprising the step of heating a catalyst precursor comprising Mo/ZSM-5 or Mo/MCM-22 at a temperature of about 500° C. for about 30 minutes in the presence of a treatment gas, wherein the treatment gas consists essentially of propane.

In a further aspect, the present invention provides the use, in a methane dehydroaromatization reaction, of a catalyst prepared according to any of the aspects of the present invention.

Preferably the pre-treatment step takes place in a continuous flow reactor. However, the pre-treatment may also occur in a batch or semi-batch reactor.

Similarly, subsequent methane dehydroaromatization using the catalyst preferably takes place in a continuous flow reactor. However, batch and semi-batch reactors can also be used.

In a further aspect, the present invention provides a process for preparing a methane dehydroaromatization catalyst comprising the step of heating a catalyst precursor comprising molybdenum oxide and an aluminosilicate in the presence of a treatment gas so as to reduce at least some of the molybdenum oxide, wherein the treatment gas comprises propane.

Preferably at least half, based on the total number of molybdenum oxide ions in the precursor catalyst before pre-treatment, more preferably at least 90%, more preferably substantially all, and most preferably all of the molybdenum oxide is reduced.

Suitably at least some, preferably at least half, based on the total number of molybdenum oxide ions in the precursor catalyst before pre-treatment, more preferably at least 90%, more preferably substantially all, and most preferably all of the molybdenum oxide is reduced to molybdenum carbide.

Preferably the molybdenum carbide comprises $Mo_2C$. Preferably the molybdenum carbide consists essentially of, and more preferably consists of $Mo_2C$.

Thus, in this aspect of the invention, the preparation of the catalyst with treatment gas comprising propane suitably produces reduced molybdenum species, preferably molybdenum carbide (especially $Mo_2C$). Some or all of the reduced molybdenum species, molybdenum carbide and $Mo_2C$ may be responsible for the methane dehydroaromatization activity of the catalyst.

Preferably the process of the present invention includes the additional step of carrying out methane dehydroaromatization using the catalyst. The present invention therefore provides a process of methane dehydroaromatization comprising the step of preparing the catalyst by heating a catalyst precursor in the presence of a treatment gas as described herein and then carrying out methane dehydroaromatization using the catalyst.

In a further aspect, the present invention provides a process of methane dehydroaromatization comprising the use of a catalyst prepared according to the present invention.

The step of carrying out dehydroaromatization using the catalyst is referred to herein as the "reaction step".

Thus, preferably, the process includes a reaction step in which a dehydroaromatization reaction is carried out using the catalyst.

Suitably, the reaction step is non-oxidative, i.e. non-oxidative methane dehydroaromatization.

Suitably, the reaction step includes supplying reaction gas selected from C1 to C5 hydrocarbons to the catalyst at a temperature of at least 600° C.

Preferably the reaction gas is selected from C1 to C5 alkanes. More preferably the reaction gas comprises methane. More preferably the reaction gas consists substantially of, more preferably consists essentially of, and most preferably consists of methane.

The reaction gas may include a mixture of gases, for examples a mixture of C1 to C5 hydrocarbons and/or a C1 to C5 hydrocarbon and $H_2$.

Thus, the present invention preferably provides a process comprising the steps of (i) supplying propane to a catalyst precursor so as to prepare a catalyst as described herein, and then (ii) supplying methane to the catalyst under methane dehydroaromatization conditions.

In other words, the pre-treatment step is preferably followed by the reaction step.

Suitably the reaction step includes supplying the reaction gas at a pressure of about one atmosphere (approximately 0.1 MPa).

Preferably the temperature of the reaction step is at least 650° C., more preferably at least 675° C., more preferably at least 690° C. and most preferably at least about 700° C. The reaction may be carried out at a temperature up to about 850° C., preferably up to about 825° C., and most preferably up to about 800° C. A particularly preferred range of temperatures is about 675° C. to about 825° C., more preferably about 700° C. to about 800° C.

In embodiments, the reaction step occurs in the same reaction vessel as the pre-treatment step. In this way, there is no need to transfer the catalyst between vessels. An additional advantage is that the catalyst can be used in the reaction step only a short time after pre-treatment, thereby taking full advantage of the improved properties of the pre-treated catalyst. Indeed, it is preferred that the reaction step occurs after the pre-treatment step without any intervening steps. Preferably the pre-treatment step and the reaction step occur in the same continuous flow reactor.

Suitably the supply of treatment gas is stopped before or shortly after the supply of reaction gas begins. Preferably the reaction gas comprises methane and the methane is supplied to the catalyst substantially in the absence of propane, preferably in the absence of propane.

Suitably the reaction step occurs at a higher temperature than the pre-treatment step. The process therefore preferably includes the step of increasing the temperature after pre-treatment.

Preferably the process includes an additional step in which, after the reaction step, treatment gas comprising propane is supplied to the catalyst at a temperature of at least 300° C. In this way, the catalyst can be re-activated after its use in methane dehydroaromatization.

The additional step of reactivating the catalyst with propane is referred to herein as the "re-activation step".

Suitably the reaction step and the reactivation step are repeated, preferably at least twice. In this way the useful life of the catalyst can be increased. Suitably this means that the frequency with which the catalyst needs to be changed is reduced.

In a further aspect, the present invention provides a process of maintaining the activity of a methane dehydroaromatization catalyst, wherein the process includes the step of supplying a treatment gas to the catalyst during methane dehydroaromatization, wherein the treatment gas comprises propane.

By "maintaining the activity" as used in this aspect it is meant that the methane dehydroaromatization activity of the catalyst is higher during at least some, and preferably most, of the methane dehydroaromatization reaction as compared to the reaction being conducted in the absence of the treatment gas.

In this aspect, the catalyst stability can be improved by supplying propane at the same time as methane dehydroaromatization is taking place. Thus, "in-situ" treatment of the catalyst can be effected. Simultaneous supply of treatment gas and reaction gas (methane) can therefore result in improved catalyst activity during the reaction as compared to reaction gas only.

In a related aspect, the process of the first aspect can be applied to a used catalyst so as to re-activate the used catalyst. In that aspect, the catalyst precursor is a used catalyst, as discussed below.

In a further aspect, the present invention provides a process of reactivating a used catalyst, which used catalyst has been used in a methane dehydroaromatization reaction and comprises molybdenum and an aluminosilicate, the process including the step of heating the used catalyst at a temperature of at least 300° C. in the presence of a treatment gas, wherein the treatment gas comprises propane.

Typically the used catalyst comprises, on some or all of its surface, a coke deposit. As noted above, the formation or build-up of coke on the catalyst occurs after use of the catalyst in methane dehydroaromatization and so a coke deposit is characteristic of a used catalyst. Typically a used catalyst has lower catalytic activity than a catalyst. Specifically, a used catalyst is suitably characterised in having a lower benzene yield than a catalyst.

In a further aspect, the present invention provides a methane dehydroaromatization catalyst prepared according to the following process: heating a catalyst precursor comprising molybdenum and an aluminosilicate at a temperature of at least 300° C. in the presence of a treatment gas, wherein the treatment gas comprises propane.

In a further aspect, the present invention provides a methane dehydroaromatization catalyst comprising molybdenum and an aluminosilicate, characterised in that the catalyst has an Activity Preservation Ratio of at least 40%, based on benzene yield as measured after 15.5 hours of methane dehydroaromatization at 700° C.

Preferably the catalyst has an Activity Preservation Ratio of at least 50%, more preferably at least 60%, more preferably at least 70% and most preferably at least 80%.

In a further aspect, the present invention provides a methane dehydroaromatization catalyst comprising molybdenum and an aluminosilicate, characterised in that the catalyst provides, in a methane dehydroaromatization reaction at 700° C., a benzene yield of at least 3.5%.

Preferably the catalyst provides a benzene yield of at least 4%, more preferably at least 4.5%, more preferably at least 5%, more preferably 5.5% and most preferably at least 6%.

In a further aspect, the present invention provides the use of a treatment gas in a process of preparing a methane dehydroaromatization catalyst, the process comprising the step of heating a catalyst precursor comprising molybdenum and an aluminosilicate at a temperature of at least 300° C. in the presence of the said treatment gas, wherein the treatment gas comprises propane.

In a further aspect, the present invention provides the use of a treatment gas in a process of preparing a methane dehydroaromatization catalyst, the process comprising the step of heating a catalyst precursor comprising molybdenum and an aluminosilicate in the presence of the said treatment gas, wherein the treatment gas comprises propane, so that the catalytic methane dehydroaromatization activity of the catalyst is maintained for longer as compared to a catalyst prepared without the use of said treatment gas.

In a further aspect, the present invention provides the use of a treatment gas in a process of preparing a methane dehydroaromatization catalyst, the process comprising the step of heating a catalyst precursor comprising molybdenum and an aluminosilicate in the presence of the said treatment gas, wherein the treatment gas comprises propane so as to reduce the rate at which, in a subsequent methane dehydroaromatization reaction, coking of the catalyst occurs, as compared to a catalyst prepared without the use of said treatment gas.

In a further aspect, the present invention provides the use of a treatment gas in a process of preparing a methane dehydroaromatization catalyst, the process comprising the step of heating a catalyst precursor comprising molybdenum and an aluminosilicate in the presence of the said treatment gas, wherein the treatment gas comprises propane, so as to provide the catalyst with an Activity Preservation Ratio of at least 40%, as measured after 15.5 hours of methane dehydroaromatization at 700° C.

In a further aspect, the present invention provides the use of a treatment gas in a process of preparing a methane dehydroaromatization catalyst, the process comprising the step of heating a catalyst precursor comprising molybdenum and an aluminosilicate in the presence of the said treatment gas, wherein the treatment gas comprises propane, so that the catalyst provides, in a methane dehydroaromatization reaction at 700° C., a benzene yield of at least 3.5%.

In a further aspect, the present invention provides the use of a treatment gas in a process of removing some or all of a coke deposit formed on a methane dehydroaromatization catalyst comprising molybdenum and an aluminosilicate.

Any one or more of the aspects of the present invention may be combined with any one or more of the other aspects of the present invention. Similarly, any one or more of the features and optional features of any of the aspects may be applied to any one of the other aspects. Thus, the discussion herein of optional and preferred features may apply to some or all of the aspects. In particular, optional and preferred features relating to the treatment gas, temperature, pressure, duration and the composition of the catalyst precursor apply to all of the other aspects. Furthermore, optional and preferred features associated with a process, method or use may also apply to a product, in particular a catalyst, and vice versa.

Definitions

The term "aluminosilicate" as used herein will be familiar to the skilled reader and pertains to natural and/or synthetic inorganic structures comprising aluminium, silicon and oxygen. Similarly, the term "zeolite" as used herein will be familiar to the skilled reader and pertains to aluminosilicates, natural and synthetic, having an "open" structure that can accommodate a variety of cations.

The terms "zeolite framework type" and "framework type" will be familiar to the skilled reader and pertain to the classification system applied by The Structure Commission of the International Zeolite Association (IZA) for identifying zeolite structures, which classification system is approved by IUPAC. The classification system assigns a Framework Type Code (FTC) to each of over 170 different zeolite framework topologies.

Detailed information about Framework Type Codes can be found on the IZA's web page, at www.iza-structure.orq/. Many of these Framework Type Codes are reproduced in Ch. Baerlocher, W. M. Meier and D. H. Olson, Atlas of Zeolite Framework Types, 5th revised edition, Elsevier, Amsterdam, 2001.

Relevant to the present invention are Framework Types MFI and MWW, both of which are known to the skilled reader.

Similarly, the preferred zeolite structures of ZSM-5 and MCM-22 are known to the skilled reader, as are methods for preparing such zeolites. The term "ZSM-5" is interchangeable with "HZSM-5", both of which denote the protonated form of the zeolite. Similarly, the terms "MCM-22" and "HMCM-22" are interchangeable.

The terms "dehydroaromatization" and "methane dehydroaromatization" as used herein will be familiar to the skilled reader and pertain to the formation of aromatic compounds, particularly benzene, from a reaction gas comprising C1 to C5 hydrocarbons and/or methane. In particular, the skilled reader will understand that in the case of methane dehydroaromatization, the reaction gas may comprise one or more other gases, e.g. C1 to C5 hydrocarbons, in addition to methane.

The term "Si/2Al ratio" as used herein will be familiar to the skilled reader and pertains to the relative number of silicon ions and twice the number of aluminium ions in the aluminosilicate.

The term "non-oxidative methane dehydroaromatization" as used herein will be familiar to the skilled reader and pertains to the reaction discussed above carried out in the absence of an oxidising species. Indeed, references herein to methane dehydroaromatization include non-oxidative methane dehydroaromatization, which is preferred.

DETAILED DESCRIPTION OF EMBODIMENTS OF THE INVENTION

The following methods were used in the examples of the present invention.
(1) Catalyst Preparation The catalysts precursors were prepared by impregnation of the appropriate zeolite (ZSM-5 or MCM-22) with the calculated amount of ammonium molybdate solution, followed by drying and calcination.
(2) Catalyst Pre-treatment Pre-treatment was carried out in a fixed bed reactor at atmospheric pressure with 300 mg of catalyst for the selected pre-treatment time and at the selected pre-treatment temperature.
(3) Catalyst Testing The test reaction (methane dehydroaromatization) was carried out in a fixed bed reactor at atmospheric pressure with 300 mg of catalyst. The reaction products were analysed and identified using gas chromatography.

Catalyst performance was measured with reference to the Activity Preservation Ratio (APR) and Benzene yield (BZ-yield).

APR was calculated as follows:

$$APR\ (\%) = BZ\text{-yield at time on stream (TOS)/Maximum } BZ\text{-yield}$$

References to APR herein are taken to be based on measurements made after 15.5 hours unless stated otherwise.

Benzene yield was calculated as follows:

$$BZ\text{-yield} = \text{benzene (produced)/methane (fed)}/6$$

EXAMPLES 1 to 4 and COMPARATIVE EXAMPLES 1 to 6

The ratio of Si/2Al in the aluminosilicate ZSM-5 support was adjusted in accordance with techniques known to the skilled reader.

Precursor Mo/ZSM-5 catalysts were prepared from ZSM-5 and molybdenum precursor by impregnation with ammonium molybdate solution, followed by drying and calcination.

Promoters in the form of Pd, Zn and Ga were incorporated into some of the catalysts using the same method as used to prepare the Mo/ZSM-5 catalyst except that corresponding metals salts were used in place of ammonium molybdate and Mo-modified zeolites in place of zeolite ZSM-5. This and other conventional techniques for incorporating a promoter into an aluminosilicate are known to the skilled reader.

The precursor catalysts were designated catalysts A to D, as follows:

Catalyst A: 12% Mo/ZSM-5(30)
Catalyst B: 12% Mo-3% Ga/ZSM-5(30)
Catalyst C: 12% Mo-3% Zn/ZSM-5(30)
Catalyst D: 12% Mo-1% Pd/ZSM-5(30).

The number in parentheses indicates the Si/2Al ratio of the ZSM-5 support.

For examples 1 to 4, each of catalysts A to D was then subjected to a pre-treatment process in accordance with the present invention. The catalyst (300 mg) was loaded into a continuous flow reactor, heated to the pre-treatment temperature of 500° C. and propane was supplied to the catalyst at a flow rate of 8 ml/min at a pressure of 0.1 MPa. Pre-treatment was carried out for 30 minutes.

For comparative examples 1 and 2, catalyst A was subjected to pre-treatment at 500° C. for 30 minutes in methane and $H_2$ respectively, at a flow rate of 7.5 ml/min. The same reactor was used as for examples 1 to 5.

For comparative examples 3 to 6, each of catalysts A to D was subjected to pre-treatment in at 700° C. for 40 minutes in He, at a flow rate of 10 ml/min. The same reactor was used as for examples 1 to 5.

Each of the pre-treated catalysts from examples 1 to 4 and comparative examples 1 to 6 was then tested for methane dehydroaromatization activity. For each pre-treated catalyst (300 mg), methane was supplied to the reaction vessel at a flow rate of 7.5 ml/min and at a pressure of 0.1 MPa. Reaction temperature was 700° C. Reaction products were detected and quantified using gas chromatography, with reference to previous measurements made in respect of known reaction products.

The results of the testing of the pre-treated catalysts are set out below in table 1.

TABLE 1

Catalytic dehydroaromatization of methane over Mo/ZSM-5 with and without $C_3H_8$ pre-treatment

| | Catalyst[a] | Treatment[b] | Benzene yield (%) | APR (%)[c] |
|---|---|---|---|---|
| Ex. 1 | A | $C_3H_8$ (8), 500° C., 30 min | 5.2 | 82 |
| Ex. 2 | B | $C_3H_8$ (8), 500° C., 30 min | 5.2 | 57 |
| Ex. 3 | C | $C_3H_8$ (8), 500° C., 30 min | 5.6 | 73 |
| Ex. 4 | D | $C_3H_8$ (8), 500° C., 30 min | 3.8 | 51 |
| Cp. 1 | A | $CH_4$ (7.5), 500° C., 30 min | 3.2 | 63[d] |
| Cp. 2 | A | $H_2$ (7.5), 500° C., 30 min | 3.6 | 41 |
| Cp. 3 | A | He (10), 700° C., 40 min | 1.1 | 9[e] |
| Cp. 4 | B | He (10), 700° C., 40 min | 0.8 | 22 |
| Cp. 5 | C | He (10), 700° C., 40 min | 0.7 | 5 |
| Cp. 6 | D | He (10), 700° C., 40 min | 1.2 | 37 |

[a]Catalyst A: 12% Mo/ZSM-5(30), Catalyst B: 12% Mo-3% Ga/ZSM-5(30), Catalyst C: 12% Mo-3% Zn/ZSM-5(30), Catalyst D: 12% Mo-1% Pd/ZSM-5(30). Note: the number in the parentheses indicates the Si/2Al ratio of ZSM-5 support.
[b]The figures in parentheses are flow rate (ml/min).
[c]APR (Activity Preservation Ratio): after 15.5 h.
[d]APR after 7.5 h.
[e]APR after 11.5 h.

EXAMPLES 5 and 6 and COMPARATIVE EXAMPLES 7 to 10

Precursor Mo/MCM-22 catalysts were prepared from MCM-22 and a molybdenum precursor by impregnation with ammonium molybdate solution, followed by drying and calcination.

The ratio of Si/2Al in the aluminosilicate MCM-22 support was adjusted in accordance with techniques known to the skilled reader.

The precursor catalysts were designated catalysts E and F, as follows:

Catalyst E: 12% Mo/MCM-22 (19)
Catalyst F: 12% Mo/MCM-22 (25)

The number in parentheses indicates the Si/2Al ratio of MCM-22 support.

For examples 5 and 6, each of catalysts E and F were subjected to a pre-treatment process in accordance with the present invention. The catalyst (300 mg) was loaded into a continuous flow reactor, heated to the pre-treatment temperature of 500° C. and propane was supplied to the catalyst at a flow rate of 8 ml/min at a pressure of 0.1 MPa. Pre-treatment was carried out for 30 minutes.

For comparative examples 7 and 8, catalyst E was subjected to pre-treatment at 500° C. for 30 minutes in methane and $H_2$ respectively, at a flow rate of 7.5 ml/min. The same reactor was used as for examples 5 and 6.

For comparative example 9, catalyst E was subjected to pre-treatment at 700° C. for 40 minutes in He, at a flow rate of 10 ml/min. The same reactor was used as for examples 5 and 6.

For comparative example 10, catalyst F was subjected to pre-treatment at 700° C. for 40 minutes in He, at a flow rate of 10 ml/min. The same reactor was used as for examples 5 and 6.

Each of the pre-treated catalysts from examples 5 and 6 and comparative examples 7 to 10 was then tested for methane dehydroaromatization activity. For each pre-treated catalyst (300 mg), methane was supplied to the reaction vessel at a flow rate of 7.5 ml/min and at a pressure of 0.1 MPa. Reaction temperature was 700° C. Reaction products were detected and quantified using gas chromatography, with reference to previous measurements made in respect of known reaction products.

The results of the testing of the pre-treated catalysts are set out below in table 2.

TABLE 2

Catalytic dehydroaromatization of methane over Mo/MCM-22 with and without $C_3H_8$ pre-treatment

| | Catalyst[a] | Treatment[b] | Benzene yield (%) | APR (%)[c] |
|---|---|---|---|---|
| Ex. 5 | E | $C_3H_8$ (8), 500° C., 30 min | 6.6 | 42 |
| Ex. 6 | F | $C_3H_8$ (8), 500° C., 30 min | 6.3 | 71 |
| Cp. 7 | E | $CH_4$ (7.5), 500° C., 30 min | 4.8 | 33 |
| Cp. 8 | E | $H_2$ (7.5), 500° C., 30 min | 4.2 | 13 |
| Cp. 9 | E | He (10), 700° C., 40 min | 0.2 | 2 |
| Cp. 10 | F | He (10), 700° C., 40 min | 0.2 | 7 |

[a]Catalyst E: 12% Mo/MCM-22 (19), Catalyst F: 12% Mo/MCM-22 (25). Note: the number in the parentheses indicates the Si/2Al ratio of MCM-22 support.
[b]The figures in parentheses are flow rate (ml/min).
[c]APR (Activity Preservation Ratio): after 15.5 h.

The results indicate that propane pre-treatment gives higher benzene yield and better catalytic stability compared with $CH_4$ and $H_2$ pre-treatment. This applies for catalysts either with or without a promoter.

The effect from the promoter for MCM-22 supported catalysts shows the same trends as for the ZSM-5 supported catalysts.

Furthermore, the results show that pre-treatment with propane provides improved activity and catalyst stability for both ZSM-5 and MCM-22 aluminosilicates. This surprising result suggests that the pre-treatment step of the present invention is applicable to aluminosilicate catalysts independently of their structure.

Compared with He pre-treatment (700° C., 40 min), propane pre-treatment can be carried out at a lower temperature and for a shorter duration (500° C., 30 min) whilst providing higher benzene yield and good catalytic stability.

Thus, a high yield of aromatic hydrocarbons and good catalytic stability can be obtained for the catalysts using propane pre-treatment. Furthermore, energy savings can be made as a result of a lower pre-treatment temperature and shorter pre-treatment time.

Compared with methane and $H_2$ pre-treatment, the benzene yield and catalytic stability are better when propane is used at the same pre-treatment conditions.

The invention claimed is:

1. A process for preparing a methane dehydroaromatization catalyst comprising the step of heating a catalyst precursor comprising molybdenum supported on a zeolite, wherein the zeolite is selected from zeolites having a framework type MFI and zeolites having a framework type MWW, at a temperature of at least 300° C. to less than 700° C. in the presence of a treatment gas, wherein the treatment gas consists of propane.

2. A process according to claim 1, wherein the preparation occurs at a temperature in the range 450° C. to 650° C.

3. A process according to claim 1, wherein the preparation occurs at a temperature in the range 475° C. to 525° C.

4. A process according to claim 1, wherein the duration of the preparation is 10 to 100 minutes.

5. A process according to claim 1, wherein the zeolite is selected from ZSM-5 and MCM-22.

6. A process according to claim 1, wherein the catalyst precursor is selected from Mo/ZSM-5 and Mo/MCM-22.

7. A process according to claim 1, wherein the Si/2Al ratio of the zeolite is in the range 10 to 100.

8. A process according to claim 1, wherein some or all of the molybdenum is present in the form of an oxide.

9. A process according to claim 1, wherein heating the catalyst precursor in the presence of the treatment gas includes reducing some or all of the molybdenum in the catalyst precursor.

10. A process according to claim 9, wherein reducing some or all of the molybdenum includes producing $Mo_2C$.

11. A process according to claim 1, wherein the molybdenum is present in an amount, expressed as a percentage of the total weight of the catalyst precursor, of at least 1%.

12. A process according to claim 1, wherein the catalyst precursor includes a promoter selected from the group consisting of Ga, Zn, Nb, Zr, La, Co, Fe, Ce, Ag, Y, V, Sr, W, Yb, Sm, Ni, Ru, Rh, Pt, Cu, Au, Al, Ti, Pb, Re, Ir, Si, Sn and Pd.

13. A process according to claim 1, wherein the pressure of the treatment gas is in the range 0.05MPa to 5MPa.

14. A process for preparing a methane dehydroaromatization catalyst comprising the step of heating a catalyst precursor comprising Mo/ZSM-5 or Mo/MCM-22 at a temperature in the range of 450° C. to 550° C. in the presence of a treatment gas, wherein the treatment gas consists of propane.

15. A process for preparing a methane dehydroaromatization catalyst comprising the step of heating a catalyst precursor comprising Mo/ZSM-5 or Mo/MCM-22 at a temperature in the range of 450° C. to 550° C. for about 10 to 50 minutes in the presence of a treatment gas, wherein the treatment gas consists of propane.

16. A process for preparing a methane dehydroaromatization catalyst comprising the step of heating a catalyst precursor comprising Mo/ZSM-5 or Mo/MCM-22 at a temperature in the range of 450° C. to 550° C. for about 10 to 50 minutes in the presence of a treatment gas, wherein Mo is present in an amount of at least 10 wt % based on the total weight of the catalyst precursor and the treatment gas consists of propane.

17. A process of methane dehydroaromatization comprising a reaction step in which a methane dehydroaromatization reaction is carried out using a catalyst prepared according to claim 1.

18. A process according to claim 17, wherein the reaction step includes supplying methane to the catalyst at a temperature in the range 675° C. to 825° C. and wherein the process includes, after the reaction step, a re-activation step in which treatment gas comprising at least 50 mol % propane is supplied to the catalyst at a temperature of at least 300° C.

19. A process of maintaining the activity of a methane dehydroaromatization catalyst, wherein the process includes the step of supplying a treatment gas to the catalyst during methane dehydroaromatization, wherein the dehydroaromatization catalyst comprises the catalyst prepared according to claim 1 and the treatment gas comprises at least 50 mol % propane.

20. A process of reactivating a used catalyst, which used catalyst has been used in the methane dehydroaromatization process of claim 17, the process including the step of heating the used catalyst at a temperature of at least 300° C. in the presence of a treatment gas, wherein the treatment gas comprises at least 50 mol % propane.

21. A methane dehydroaromatization catalyst prepared according to the process of claim 1.

22. A methane dehydroaromatization catalyst according to claim 21, wherein the catalyst comprises molybdenum and an aluminosilicate, characterised in that the catalyst has an Activity Preservation Ratio of at least 40%, based on benzene yield as measured after 15.5 hours of methane dehydroaromatization at 700° C.

23. A methane dehydroaromatization catalyst according to claim 21, wherein the catalyst comprises molybdenum and an aluminosilicate, characterised in that the catalyst provides, in a methane dehydroaromatization reaction at 700° C., a benzene yield of at least 3.5%.

24. Use of a treatment gas in a process of preparing a methane dehydroaromatization catalyst, the process comprising the step of heating a catalyst precursor comprising molybdenum supported on a zeolite, wherein the zeolite is selected from zeolites having a framework type MFI and zeolites having a framework type MWW, in the presence of the said treatment gas, wherein the treatment gas consists of propane, so that the catalytic methane dehydroaromatization activity of the catalyst is maintained for longer as compared to a catalyst prepared without the use of said treatment gas.

25. A process for preparing a methane dehydroaromatization catalyst comprising the step of heating a catalyst precursor comprising molybdenum and a zeolite, at a temperature of at least 300° C. in the presence of a treatment gas, wherein the treatment gas consists of propane and wherein the catalyst has an activity preservation ratio of at least 40% based on benzene yield as measured after 15.5 hours of methane dehydroaromatization at 700° C.

* * * * *